(12) United States Patent
Nakazono et al.

(10) Patent No.: US 10,347,998 B2
(45) Date of Patent: Jul. 9, 2019

(54) CRIMP TERMINAL, ELECTRIC WIRE WITH CRIMP TERMINAL, AND MEDICAL DEVICE SENSOR

(71) Applicant: TATSUTA Electric Wire & Cable Co., Ltd., Higashiosaka-shi (JP)

(72) Inventors: Syoji Nakazono, Kizugawa (JP); Kiyotaka Urashita, Kizugawa (JP)

(73) Assignee: TATSUTA Electric Wire & Cable Co., Ltd., Osaka (JP)

( * ) Notice: Subject to any disclaimer, the term of this patent is extended or adjusted under 35 U.S.C. 154(b) by 0 days.

(21) Appl. No.: 16/020,207

(22) Filed: Jun. 27, 2018

(65) Prior Publication Data

US 2019/0006772 A1  Jan. 3, 2019

(30) Foreign Application Priority Data

Jun. 28, 2017 (JP) ................................ 2017-126232
Feb. 26, 2018 (JP) ................................ 2018-032268

(51) Int. Cl.
| | |
|---|---|
| *H01R 4/18* | (2006.01) |
| *A61B 5/00* | (2006.01) |
| *H01R 13/52* | (2006.01) |
| *H01R 13/11* | (2006.01) |

(52) U.S. Cl.
CPC .............. *H01R 4/188* (2013.01); *A61B 5/68* (2013.01); *H01R 4/184* (2013.01); *H01R 13/5224* (2013.01); *H01R 13/111* (2013.01); *H01R 2201/12* (2013.01)

(58) Field of Classification Search
CPC .... H01R 4/188; H01R 4/184; H01R 13/5224; H01R 2201/12; H01R 4/18–4/20; H01R 13/111; A61B 5/68

USPC ......................................... 439/877, 878, 909
See application file for complete search history.

(56) References Cited

U.S. PATENT DOCUMENTS

| | | | | |
|---|---|---|---|---|
| 2,762,022 A | * | 9/1956 | Benander ............... | H01R 13/28 439/290 |
| 3,200,367 A | * | 8/1965 | Blanchenot .......... | H01R 13/113 439/716 |
| 4,934,965 A | | 6/1990 | Buddrus et al. | |
| 5,033,982 A | | 7/1991 | Lucas | |

(Continued)

FOREIGN PATENT DOCUMENTS

| | | |
|---|---|---|
| JP | 4996474 U1 | 8/1974 |
| JP | 201073346 A | 4/2010 |

*Primary Examiner* — Travis S Chambers
(74) *Attorney, Agent, or Firm* — The Webb Law Firm

(57) ABSTRACT

Provided is a crimp terminal including an electric wire connector connectable to an electric wire. The electric wire connector includes a body, a plurality of first crimping pieces extending from a first end of the body, and at least one second crimping piece extending from a second end thereof. The first and second crimping pieces are alternately arranged while being displaced from each other. When the crimping pieces are crimped to connect a core wire of the electric wire, a clearance between one first crimping piece and the second crimping piece formed at a position closest to an insulating member of the electric wire is larger than a clearance between a remaining first crimping piece and the second crimping piece formed at another position. Also provided are an electric wire with the crimp terminal, and a medical device sensor including the electric wire with the crimp terminal.

5 Claims, 15 Drawing Sheets

(56) References Cited

U.S. PATENT DOCUMENTS

| | | | |
|---|---|---|---|
| 5,199,910 A | 4/1993 | Kahle et al. | |
| 5,863,225 A | 1/1999 | Liebich et al. | |
| 7,993,170 B2 * | 8/2011 | Nakata | H01R 4/185 |
| | | | 439/587 |
| 9,673,578 B1 * | 6/2017 | Lane | H01R 4/183 |
| 2002/0055297 A1 | 5/2002 | Feeny, Jr. | |
| 2003/0060090 A1 | 3/2003 | Allgood et al. | |
| 2011/0213274 A1 * | 9/2011 | Telfort | A61B 7/003 |
| | | | 600/586 |

* cited by examiner

CRIMP TERMINAL, ELECTRIC WIRE WITH CRIMP TERMINAL, AND MEDICAL DEVICE SENSOR

CROSS-REFERENCE TO RELATED APPLICATIONS

This application claims priority to Japanese Patent Application Nos. 2017-126232 and 2018-032268, filed Jun. 28, 2017, and Feb. 26, 2018, respectively, the disclosures of which are hereby incorporated in their entirety by reference.

FIELD OF THE INVENTION

The present invention relates to a crimp terminal connectable to an electric wire having a core wire made of conductive fibers, an electric wire with the crimp terminal, and a medical device sensor that includes the electric wire with the crimp terminal.

BACKGROUND OF THE INVENTION

A conventionally known crimp terminal includes a plurality of crimping pieces alternately arranged while being displaced from each other in a lengthwise direction to crimp a connected portion of an electric wire (see JP 2010-073346 A). Specifically, the crimp terminal includes, as shown in FIG. 13, a terminal connector 101 to which a mating terminal or the like is connected, and an electric wire connector 102 that is continuously formed with the terminal connector 101 and to which an electric wire is connected (crimped).

The electric wire connector 102 includes a bottom section 1021 extending in the same direction as that in which the core wire is arranged (a first direction), a plurality of first side crimping pieces 1022 extending from a first side edge in a second direction orthogonal to the first direction of the bottom section 1021, and a plurality of second side crimping pieces 1023 extending from a second side edge in the second direction of the bottom section 1021. The first side crimping pieces 1022 and the second side crimping pieces 1023 are alternately arranged while being displaced from each other in the first direction.

In the crimp terminal 100, the core wire exposed in a tip portion of the electric wire is arranged on the bottom section 1021, and the first side crimping pieces 1022 and the second side crimping pieces 1023 are crimped to embrace the core wire, which causes the core wire to be press-contacted to the bottom section 1021 (see FIG. 14). The electric wire is connected to the crimp terminal in this way.

The electric wire connector 102 of the crimp terminal 100 configured as above has a larger area of contact between the core wire and the crimping pieces than an electric wire connector in which pairs of crimping pieces 1022A and 1023A, each of which is arranged at the same position in the first direction, are arranged at intervals in the first direction, as shown in FIG. 15. This configuration sufficiently provides a force to retain the electric wire by the electric wire connector 102, or in other words, causes the crimped electric wire to be pulled out of the electric wire connector 102 when the electric wire is pulled in a pulling direction (i.e. pull-out strength), under the conditions where the crimping pieces are crimped with a reduced force.

Thus, the crimp terminal 100 can be used for an electric wire having a core wire made of soft metal, such as an aluminum wire, i.e. an electric wire that is likely to be broken with an increased crimping force.

In recent years, there have been some cases where an electric wire having a core wire made not of metal but of conductive fibers such as carbon fibers must be used due to restrictions imposed in certain applications thereof.

When such an electric wire is connected to the crimp terminal, the conductive fibers therein are less likely to be internally stressed at the time of applying pressures. Therefore, in order to obtain a retaining force at a portion to which such an electric wire is connected, crimping must be made with a greater pressing force than the case where the electric wire having the metal core wire that is more likely to be internally stressed is connected. Moreover, for such an electric wire, extremely thin conductive fibers (for example, about several micrometers) are used. Therefore, even if the abovementioned crimp terminal 100 is used, the conductive fibers are still likely to be broken at the time of crimping the crimping pieces 1022, 1023; thus, the crimp terminal 100 connected to the electric wire fails to obtain sufficient pull-out strength.

SUMMARY OF THE INVENTION

It is therefore an object of the present invention to provide a crimp terminal capable of securing sufficient pull-out strength when an electric wire having a core wire made of conductive fibers is crimped to an electric wire connector, an electric wire with the crimp terminal, and a medical device sensor that includes the electric wire with the crimp terminal.

The following presents a simplified summary of the invention disclosed herein in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The crimp terminal according to the present invention includes: an electric wire connector connectable to an electric wire having a core wire sheathed with an insulating member, the electric wire connector including: a body extending in a first direction that coincides with an extending direction of a portion of the electric wire to which the electric wire connector is connected; a plurality of first crimping pieces extending from a first end in a second direction orthogonal to the first direction of the body; and at least one second crimping piece extending from a second end in the second direction of the body, wherein the plurality of first crimping pieces and the at least one second crimping piece are alternately arranged while being displaced from each other in the first direction, and configured to be crimped to embrace the core wire exposed in a leading end portion of the electric wire so that the core wire is press-contacted to the body, and wherein, when the plurality of first crimping pieces and the at least one second crimping piece are crimped to connect the core wire to the electric wire connector, a first clearance in the first direction between one of the plurality of first crimping pieces and the at least one second crimping piece, the first clearance being formed at a position closest in the first direction to the insulating member of the electric wire, is larger than a second clearance in the first direction between a remaining one of the plurality of first crimping pieces and the at least one second crimping piece, the second clearance being formed at another position in the first direction.

The crimp terminal may be configured such that the first clearance has such a distance that the one of the plurality of first crimping pieces and the at least one second crimping piece having their edges expanding as a result of crimping are not in contact with each other.

The crimp terminal may be configured such that each of the plurality of first crimping pieces has a distal end portion, a proximal end portion, and an edge extending in a direction crossing the second direction between the distal end portion and the proximal end portion of each of the plurality of first crimping pieces, and that the at least one second crimping piece has a distal end portion, a proximal end portion, and an edge extending in a direction crossing the second direction between the distal end portion and the proximal end portion of the at least one second crimping piece.

An electric wire with a crimp terminal according to the present invention includes: any one of the abovementioned crimp terminals; and an electric wire configured to be connected to the electric wire connector of the crimp terminal, wherein the core wire is constituted by conductive fibers.

A medical device sensor according to the present invention includes: a medical sensor body; an output electric wire extending from the medical sensor body; and any one of the abovementioned crimp terminals, wherein the output electric wire is connected to the electric wire connector of the crimp terminal, and the output electric wire has a core wire constituted by conductive fibers.

BRIEF DESCRIPTION OF DRAWINGS

The foregoing and other features of the present invention will become apparent from the following description and drawings of an illustrative embodiment of the invention in which.

DETAILED DESCRIPTION OF THE PREFERRED EMBODIMENT

Figure 1:
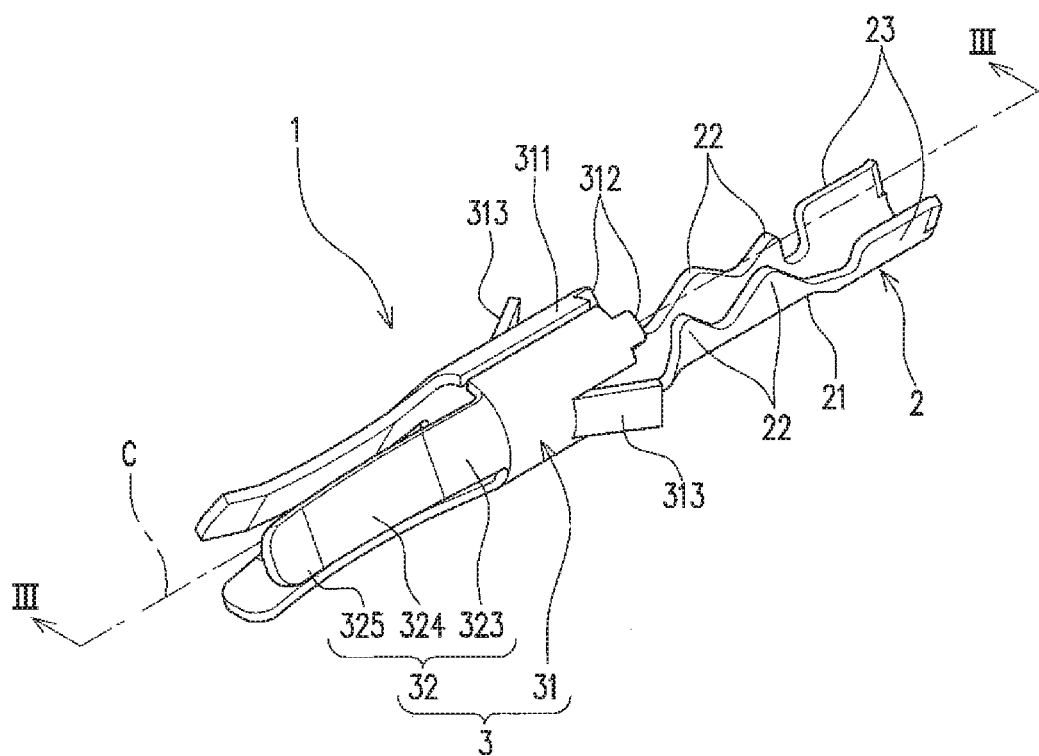
FIG. 1 is a perspective view of a connector terminal according to one embodiment.
Figure 2:
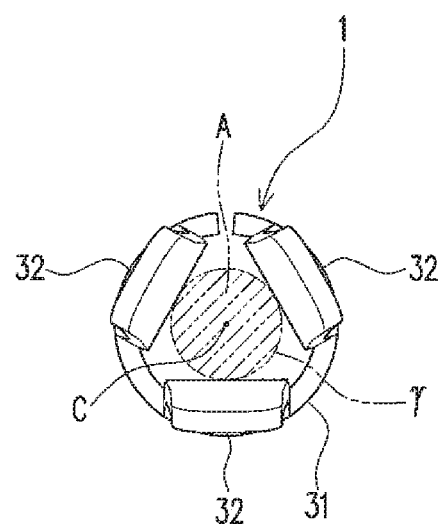
FIG. 2 is a schematic view of the connector terminal as seen from a front side in a direction of a central axis thereof.

Hereinafter, an embodiment of a crimp terminal according to the present invention will be described with reference to FIG. 1 to FIG. 9. The crimp terminal of this embodiment is a connector terminal. More specifically, the crimp terminal is a female connector terminal to which a male connector terminal pin (a mating terminal pin) is connected (fitted). An electric wire having a core wire made of conductive fibers is connectable to the connector terminal.

As shown in FIG. 1 to FIG. 4, the connector terminal 1 includes an electric wire connector 2 to which an electric wire is connectable. The connector terminal 1 also includes an electric connector 3 that is conductive to the electric wire connector 2 and to which a mating terminal pin P (see FIG. 8) is detachably connected. The connector terminal 1 of this embodiment is formed of a conductive metal sheet that is stamped out into a specific shape (see FIG. 4) and then bent into a tubular shape with an axis parallel to a centerline C1 as a central axis C. The connector terminal 1 is formed of phosphor bronze, but may also be formed of brass, nickel silver, plated stainless steel, or the like. Hereinafter, in a direction of the central axis C, an electric connector 3 side (the left side in FIG. 3) is referred to as a front side, and an electric wire connector 2 side (the right side in FIG. 3) is referred to as a rear side.

The electric wire connector 2 includes a plate-shaped body 21, a plurality of conductive crimping pieces 22 extending from the body 21, and at least a pair of sheathed part crimping pieces 23 extending from a portion of the body 21 closer to the rear side thereof than the conductive crimping pieces 22. In the connector terminal 1 before it is bent as aforementioned (i.e., it is in the state shown in FIG. 4: hereinafter referred to as "flat plate-shaped connector terminal 1"), the conductive crimping pieces 22 and the sheathed part crimping pieces 23 are portions extending from both ends in a width direction of the body 21 (i.e., a direction orthogonal to the centerline C1) toward the outside thereof in the width direction.

The body 21 is a portion extending in the direction of the central axis C and having a U-shape in a cross section taken in a direction orthogonal to the central axis C.

Figure 5:
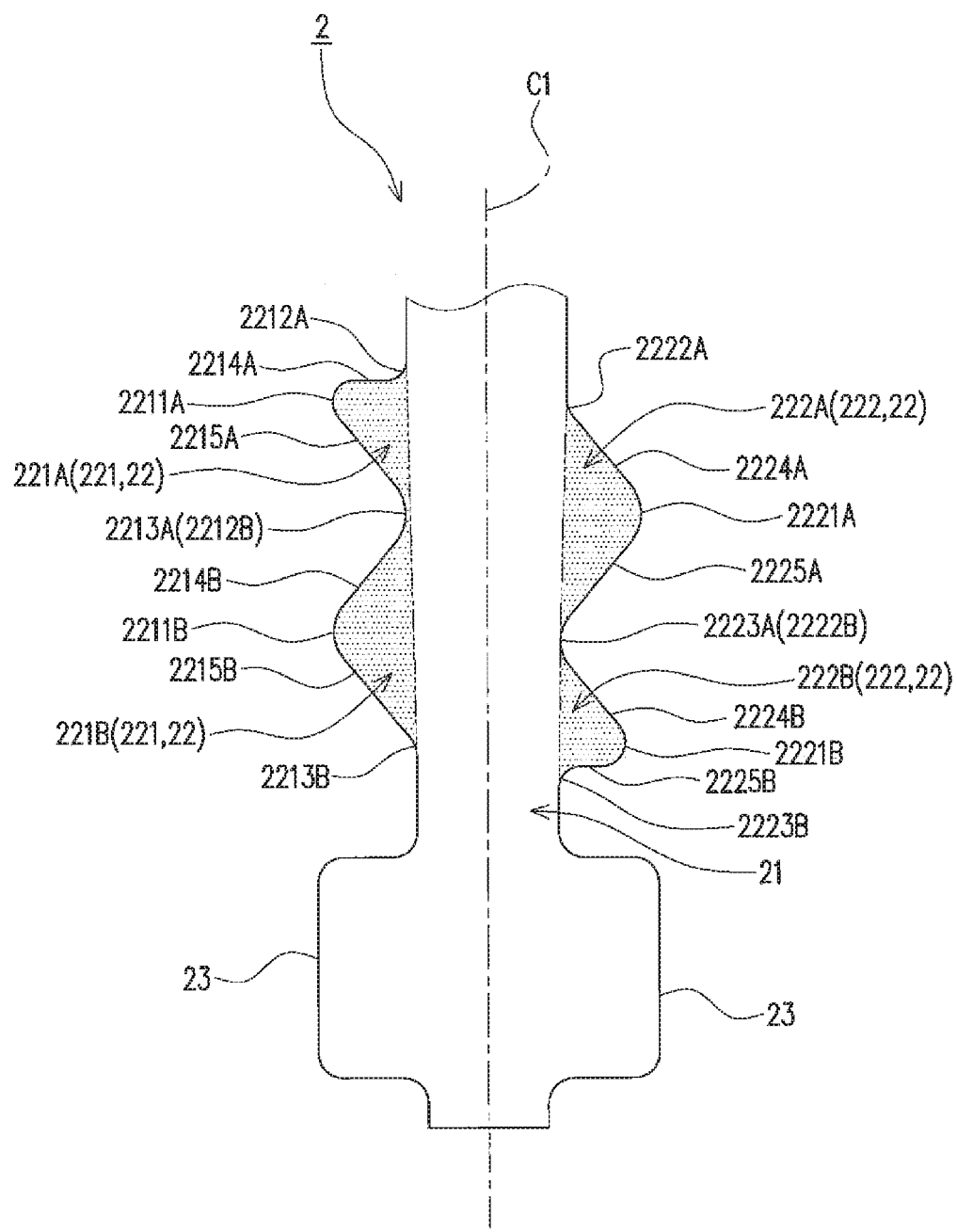
FIG. 5 is an enlarged view of an electric wire connector in the development view of the connector terminal.

The plurality of conductive crimping pieces 22 are crimped to embrace the core wire (a conductor) exposed in a leading end portion of the electric wire so that the core wire is press-contacted to the body 21. In the electric wire connector 2 of the flat plate-shaped connector terminal 1 (hereinafter referred to simply as "flat plate-shaped electric wire connector 2"), as shown in FIG. 5, the plurality of conductive crimping pieces 22 are constituted by a plurality of first crimping pieces 221 extending from a first end in the width direction of the body 21 (i.e., the left end in FIG. 5) and at least one second crimping piece 222 extending from a second end in the width direction of the same (i.e., the right end in FIG. 5). The plurality of first crimping pieces 221 and the at least one second crimping piece 222 alternately extend while being displaced from each other in the direction of the centerline C1 (i.e., they are alternately arranged). The electric wire connector 2 of this embodiment includes two first crimping pieces 221 and two second crimping pieces 222.

Out of the two first crimping pieces 221, one (front side) first crimping piece 221A has a chevron shape. Specifically, in the flat plate-shaped electric wire connector 2, the one first crimping piece 221A has a front side edge 2214A extending in the width direction of the body 21 (i.e., a direction orthogonal to the centerline C1) from the first end in the width direction. Also, in the flat plate-shaped electric wire connector 2, a rear side edge 2215A extends in a direction crossing the width direction of the body 21, specifically, in the direction away from the centerline C1 as it advances toward the front side, from the first end in the width direction. That is, in the flat plate-shaped electric wire connector 2, the front side of the one first crimping piece 221A has the edge 2214A between a distal end 2211A and a proximal end 2212A that extends in the width direction, and the rear side of the one first crimping piece 221A has the edge 2215A between the distal end (distal end portion) 2211A and a proximal end (proximal end portion) 2213A that extends in the direction crossing the width direction.

Out of the two first crimping pieces 221, the other (rear side) first crimping piece 221B also has a chevron shape. Specifically, in the flat plate-shaped electric wire connector 2, the other first crimping piece 221B has a front side edge 2214B extending in a direction crossing the width direction of the body 21, specifically, in the direction away from the centerline C1 as it advances toward the rear side, from the first end in the width direction. Also, in the flat plate-shaped electric wire connector 2, a rear side edge 2215B extends in the direction crossing the width direction of the body 21, specifically, in the direction away from the centerline C1 as it advances toward the front side, from the first end in the width direction. That is, in the flat plate-shaped electric wire connector 2, the front side of the other first crimping piece 221B has the edge 2214B between a distal end (distal end portion) 2211B and a proximal end (proximal end portion) 2212B that extends in the direction crossing the width direction, and the rear side of the other first crimping piece 221B has the edge 2215B between the distal end (distal end portion) 2211B and a proximal end (proximal end portion) 2213B that extends in the direction crossing the width direction.

The rear side proximal end 2213A of the one first crimping piece 221A and the front side proximal end 2212B of the other first crimping piece 221B coincide with each other in the direction of the centerline C1.

Out of the two second crimping pieces 222, one (front side) second crimping piece 222A has a chevron shape. Specifically, in the flat plate-shaped electric wire connector 2, the one second crimping piece 222A has a front side edge 2224A extending in a direction crossing the width direction of the body 21, specifically, in the direction away from the centerline C1 as it advances toward the rear side, from the second end in the width direction. Also, in the flat plate-shaped electric wire connector 2, a rear side edge 2225A extends in a direction crossing the width direction of the body 21, specifically, in the direction away from the centerline C1 as it advances toward the front side, from the second end in the width direction. That is, in the flat plate-shaped electric wire connector 2, the front side of the one second crimping piece 222A has the edge 2224A between a distal end (distal end portion) 2221A and a proximal end (proximal end portion) 2222A that extends in the direction crossing the width direction, and the rear side of the one second crimping piece 222A has the edge 2225A between the distal end (distal end portion) 2221A and a proximal end (proximal end portion) 2223A that extends in the direction crossing the width direction.

Out of the two second crimping pieces 222, the other (rear side) second crimping piece 222B also has a chevron shape. Specifically, in the flat plate-shaped electric wire connector 2, the other second crimping piece 222B has a front side edge 2224B extending in the direction crossing the width direction of the body 21, specifically, in the direction away from the centerline C1 as it advances toward the rear side, from the second end in the width direction. Also, in the flat plate-shaped electric wire connector 2, a rear side edge 2225B extends in the width direction of the body 21 from the second end in the width direction. That is, in the flat plate-shaped electric wire connector 2, the front side of the other second crimping piece 222B has the edge 2224B between a distal end (distal end portion) 2221B and a proximal end (proximal end portion) 2222B that extends in the direction crossing the width direction, and the rear side of the other second crimping piece 222B has the edge 2225B between the distal end 2221B and a proximal end 2223B that extends in the width direction.

The rear side proximal end 2223A of the one second crimping piece 222A and the front side proximal end 2222B of the other second crimping piece 222B coincide with each other in the direction of the centerline C1.

As to the crimping pieces 221A, 221B, 222A, and 222B of the flat plate-shaped electric wire connector 2, a height dimension (a dimension in the width direction) of the other second crimping piece 222B from the body 21 is smaller than the height dimensions of the remaining crimping pieces 221A, 221B, and 222A. Note that the remaining crimping pieces 221A, 221B, and 222A have the same height dimension.

In the flat plate-shaped electric wire connector 2, the meeting point between the two first crimping pieces 221A and 221B (the position at which the proximal end 2213A of the one first crimping piece 221A coincides with the proximal end 2212B of the other first crimping piece 221B) and the distal end 2221A of the one second crimping piece 222A are located at the same position with respect to the direction of the centerline C1. In contrast, the distal end 2211B of the other first crimping piece 221B and a meeting point between the two second crimping pieces 222A and 222B (the position at which the proximal end 2223A of the one second crimping piece 222A coincides with the proximal end 2222B of the other second crimping piece 222B) are located at different positions with respect to the direction of the centerline C1. Specifically, the distal end 2211B of the first crimping piece 221B is located closer to the front side than the meeting point between the two second crimping pieces 222A and 222B.

Figure 6:
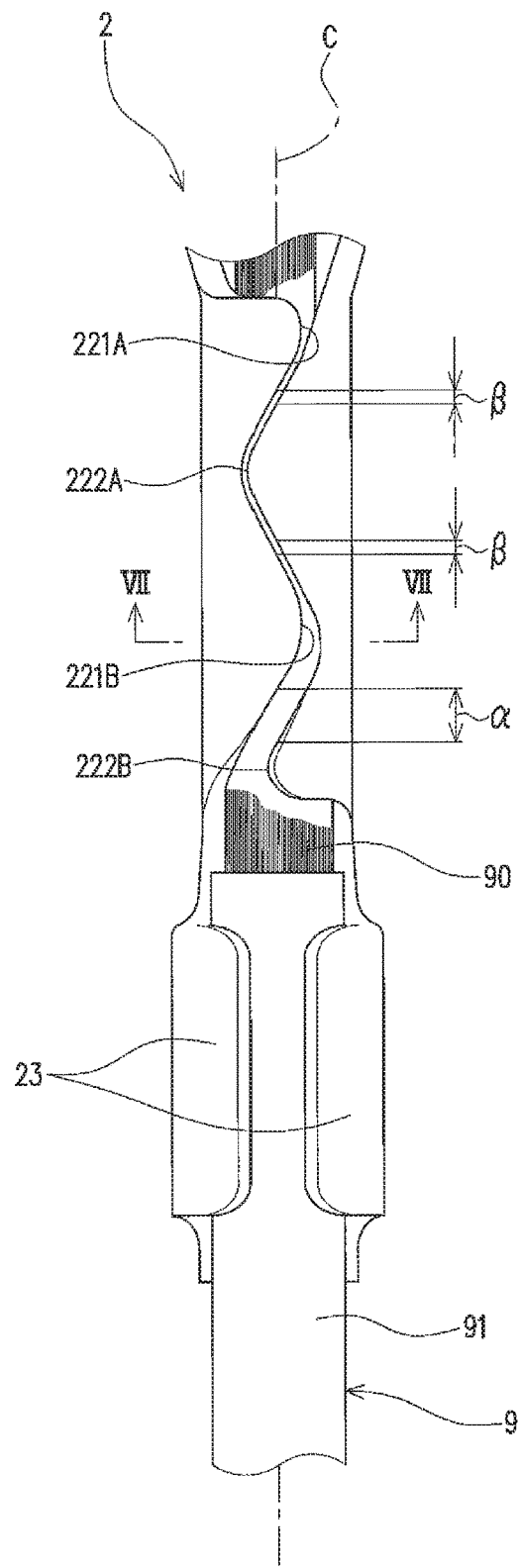
FIG. 6 is a view showing the electric wire connector to which an electric wire is connected.

When the crimping pieces 221A, 221B, 222A, and 222B configured as above are crimped so as to embrace a core wire 90 of an electric wire 9, as shown in FIG. 6, a clearance in the direction of the central axis C between the first crimping piece 221B and the second crimping piece 222B, both of which are formed on the rearmost side (the position close to an insulation sheathed member 91 of the electric wire 9), specifically, the clearance in the direction of the central axis C (a first clearance α), is larger than a clearance between each of the first crimping pieces 221A and 221B and the second crimping piece 222A (the clearance in the direction of the central axis C: a second clearance ß). More specifically, each of the first clearance α and the second clearances ß is a clearance between points (intersections) at which the opposing edges of the adjacent first crimping pieces 221A and 221B and the adjacent second crimping pieces 222A and 222B cross a virtual line parallel to the central axis C, the virtual line passing through the crimping pieces 221A, 221B, 222A, and 222B in the state of being crimped (see FIG. 6). In the connector terminal 1 of this embodiment, the clearance between the other first crimping piece 221B and the other second crimping piece 222B (the first clearance α) is larger than the clearance between the other first crimping piece 221B and the one second crimping piece 222A (the second clearance ß) and the clearance between the one first crimping piece 221A and the one second crimping piece 222A (the second clearance ß).

The first clearance α has such a distance that the first crimping piece 221B and the second crimping piece 222B having their edges expanding as a result of crimping are not in contact with each other. A more specific description is provided below.

Figure 7:
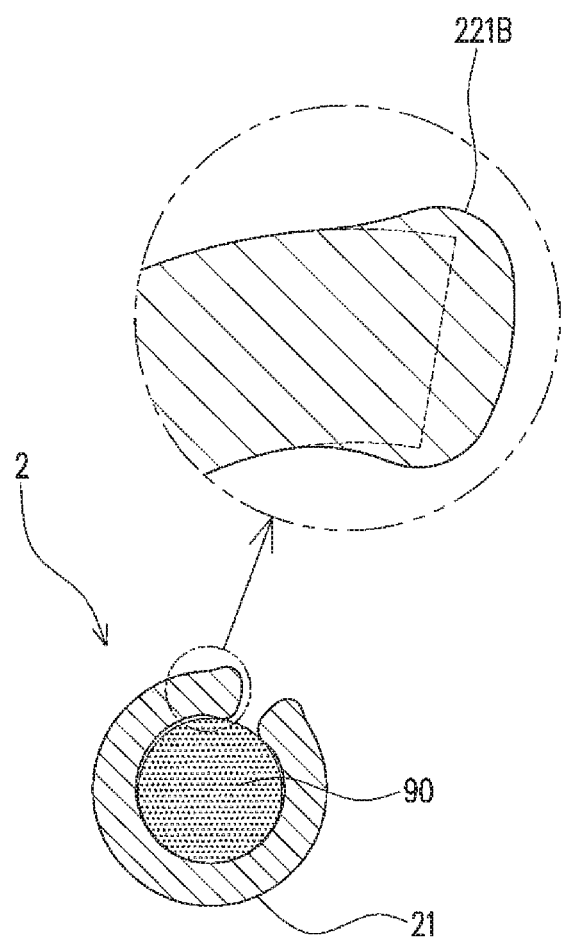
FIG. 7 is a cross sectional view taken along line VII-VII in FIG. 6.

When the crimping pieces 221A, 221B, 222A, and 222B are crimped, the edges of the crimping pieces 221A, 221B, 222A, and 222B expand compared to their initial state (i.e., the state before they are crimped: see the broken line in the partially enlarged view in FIG. 7), as shown in the cross section in FIG. 7. Further, there are some cases where the crimping pieces 221A, 221B, 222A, and 222B after being crimped are slightly displaced, for example, in the direction of the central axis C from estimated positions, depending on the conditions of the core wire 90, the electric wire 9, and the like at the time of being crimped. The first clearance α is set to such a dimension that the other first crimping piece 221B and the other second crimping piece 222B are not in contact with each other even if the abovementioned expansion, displacement, or the like occurs. As described above, the other first crimping piece 221B and the other second crimping piece 222B have such a shape as to form the first clearance α when being crimped. The first clearance α of this embodiment is made to be wider as it advances to the rear side (see FIG. 6).

Returning to FIG. 1 to FIG. 6, the at least a pair of sheathed part crimping pieces 23 are configured to be crimped to have an insulation sheathed portion of the electric wire 9 near the exposed core wire 90 sandwiched between the body 21 and the at least a pair of sheathed part crimping pieces 23. The electric wire connector 2 of this embodiment includes a pair of sheathed part crimping pieces 23. In the flat plate-shaped electric wire connector 2, the pair of sheathed part crimping pieces 23 respectively extend toward the outside in the width direction from portions adjacent to and rearward of the conductive crimping pieces 22 in the direction of the centerline C1. The sheathed part crimping piece 23 on a first side in the width direction and the sheathed part crimping piece 23 on a second side therein are both located at the same position with respect to the direction of the centerline C1.

In the flat plate-shaped connector terminal 1 that includes the body 21, the conductive crimping pieces 22, and the sheathed part crimping pieces 23, the electric wire connector 2 is formed with the body 21 bent to be curved (see FIG. 1).

The electric connector 3 includes an electric connector body 31 continuously provided with the body 21, and three or more (three in this embodiment) elastic contact pieces 32 arranged at intervals around the central axis C. The electric connector 3 is conductively connected (fitted) to the mating terminal pin P (see FIG. 8) when the mating terminal pin P is inserted into an area A (see FIG. 2) surrounded by the three or more elastic contact pieces 32.

The electric connector body 31 includes a tubular portion 311 surrounding the central axis C, and a stopper piece 312 extending from the rear end of the tubular portion 311 toward the central axis C. The electric connector body 31 also includes terminal side engagement portions 313 that extend outwardly from the tubular portion 311 and are engageable with a connector housing in the case where the connector terminal 1 is housed in the connector housing.

Figure 8:
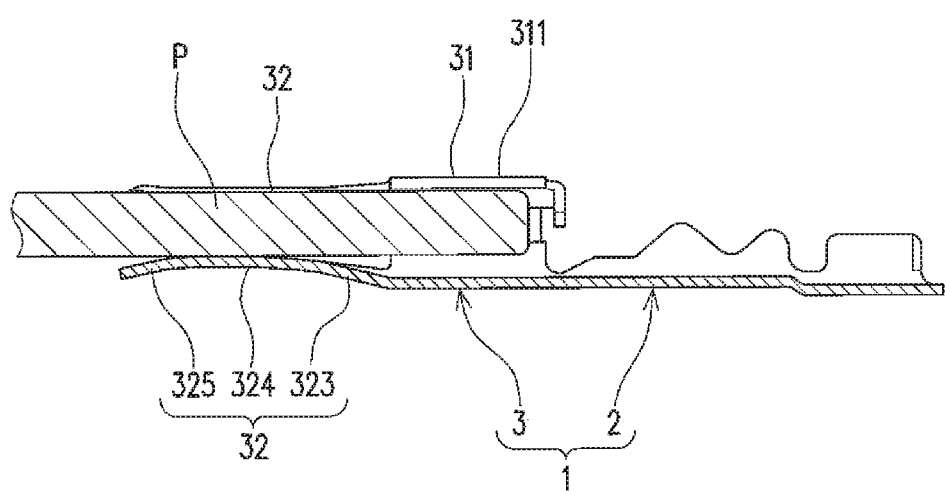
FIG. 8 is a view for illustrating the state where a mating terminal pin is connected to the connector.

The tubular portion 311 is a portion inside which a leading end portion of the mating terminal pin P is positioned (i.e. the area surrounded by the tubular portion 311) when the mating terminal pin P is fitted to the connector terminal 1 (see FIG. 8). The tubular portion 311 is formed with a rectangular plate portion of the flat plate-shaped connector terminal 1 having a shape elongated in a direction orthogonal to the centerline C1, the rectangular plate portion being entirely curved into a tubular shape so as to make the central axis C as the center and having the edges in its longitudinal direction of the rectangular plate portion opposed to each other.

The stopper piece 312 is configured to stop the leading end of the mating terminal pin P from moving further into the inside of the connector terminal 1 (toward the rear side of the connector terminal 1) when the mating terminal pin P is fitted to the connector terminal 1. That is, the stopper piece 312 is configured to abut the leading end of the mating terminal pin P when the mating terminal pin P moving along the central axis C enters the tubular portion 311 to thereby prevent the leading end of the mating terminal pin P from moving further into the inside of the connector terminal 1.

Figure 4:
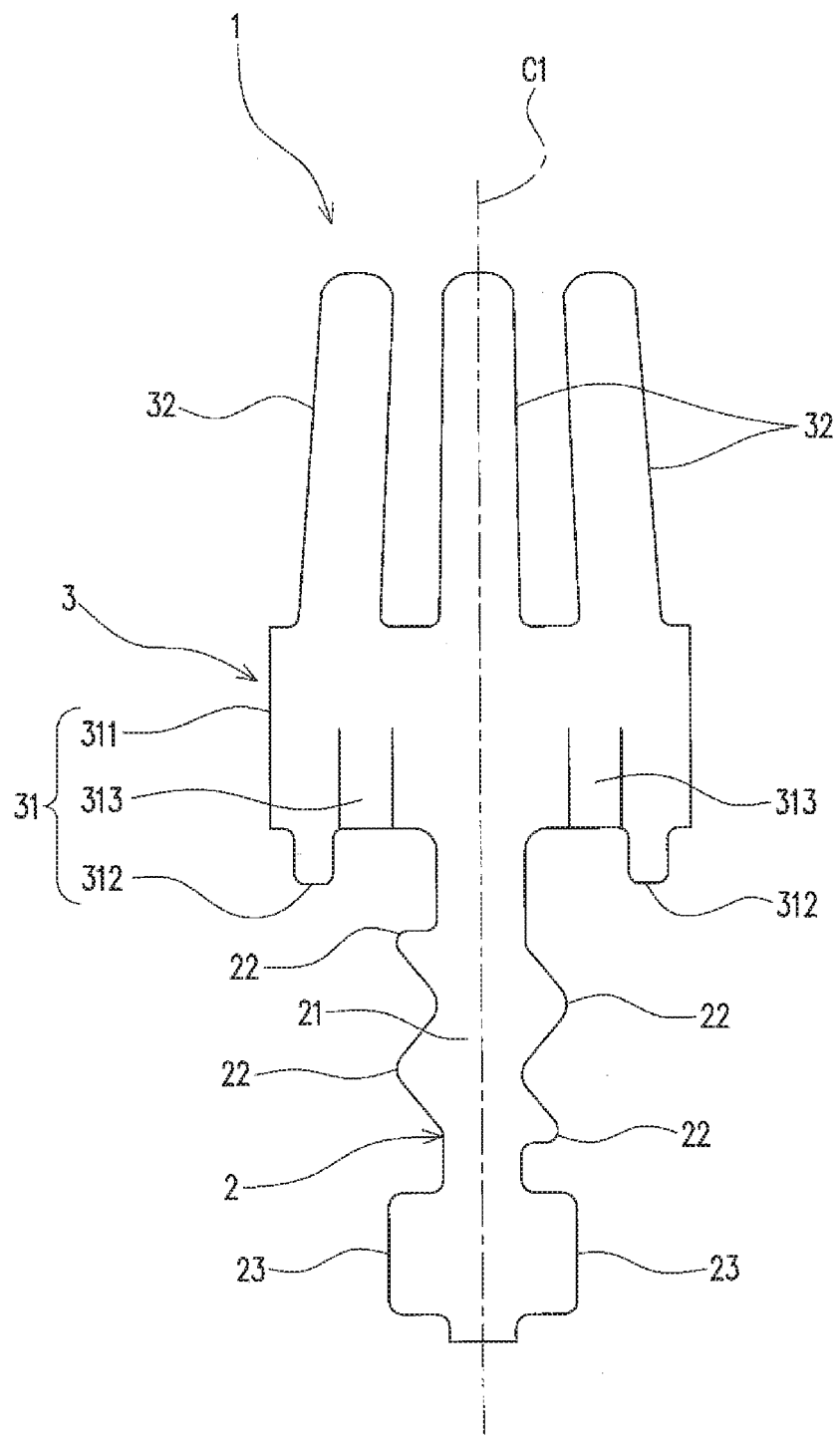
FIG. 4 is a development view of the connector terminal.

The stopper piece 312 is formed with a portion extending in the direction of the centerline C1 from the rear side end edge of the flat plate-shaped tubular portion 311 shown in FIG. 4, the portion being bent toward the central axis C in the state where the tubular portion 311 is in a tubular shape. In the electric connector 3 of this embodiment, a plurality of stopper pieces 312 are arranged at intervals in a circumferential direction of the tubular portion 311.

The terminal side engagement portions 313 are portions that engage with a connector housing 5 (see FIG. 10) in the case where the connector terminal 1 is housed in the connector housing 5. The terminal side engagement portions 313 project from the tubular portion 311 and are inclined with respect to the central axis C so as to be away from the central axis C as they advance toward the rear side.

The three elastic contact pieces 32 extend along the central axis C, are pressed by the mating terminal pin P when the mating terminal pin P is inserted along the central axis C into the area A surrounded by the elastic contact pieces 32, and are thereby elastically deformed. The elastic contact pieces 32 are arranged at intervals from each other on the circumference of a circle with the central axis C as the center. A specific configuration of each of the elastic contact pieces 32 is described as follows.

The elastic contact pieces 32 are elastically-deformable plate-shaped portions that extend from the electric connector body 31 toward the front side, and are arranged at equal intervals around the central axis C, with their main surfaces (i.e., surfaces orthogonal to a thickness direction thereof) 32A directed to the central axis C. Each of the elastic contact pieces 32 has two bent portions (a first bent portion 321 and a second bent portion 322) arranged at an interval from each other in the direction of the central axis C. Hereinafter, a portion of the elastic contact piece 32 rearward of the first bent portion 321 is referred to as a base portion 323, a portion thereof between the first bent portion 321 and the second bent portion 322 is referred to as a contact portion 324, and a portion thereof forward of the second bent portion 322 is referred to as a leading end portion 325.

Figure 3:
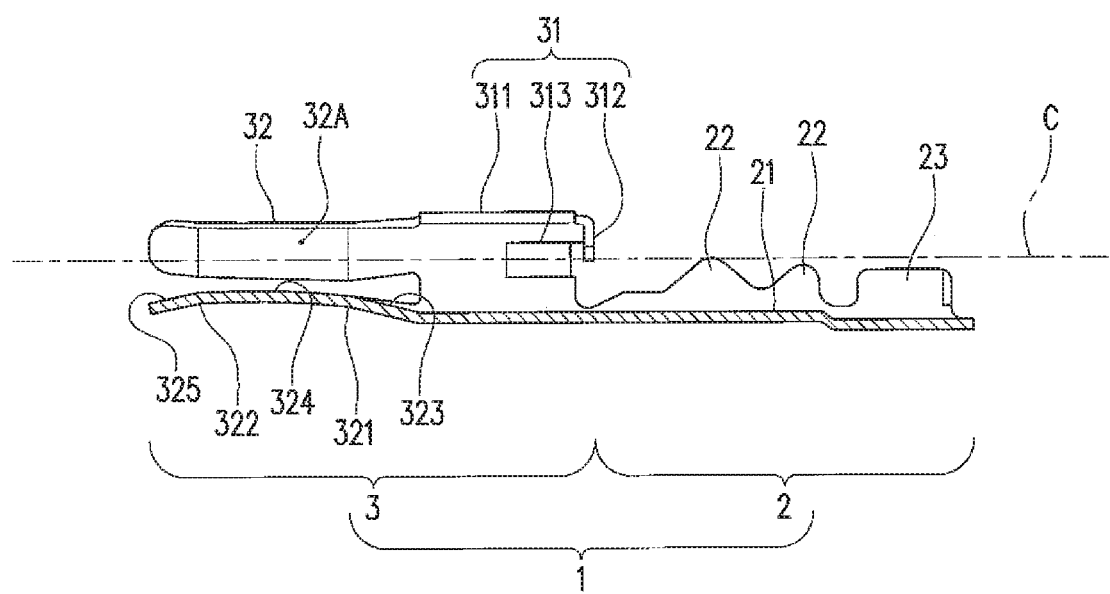
FIG. 3 is a cross sectional view taken along line III-III in FIG. 1.

The base portion 323 is inclined with respect to the central axis C so as to be away from the central axis C as it advances from the contact portion 324 toward the rear side (see FIG. 3).

The contact portion 324 is a portion that is in contact (conduction) with the mating terminal pin P when the mating terminal pin P is inserted along the central axis C into the area A surrounded by the three elastic contact pieces 32 (see FIG. 8). The contact portion 324 is deflectable. Specifically, the contact portion 324 extends along the central axis C and is curved in such a direction as to project toward the central axis C. With this curving, an inscribed circle y (see FIG. 2) that is centered at the central axis C and tangent to a portion of each of the contact portions 324 closest to the central axis C is made smaller than the outer circumference of the mating terminal pin P. This configuration causes the contact portions 324 to be pressed in a direction away from the central axis C by the mating terminal pin P that is inserted into the area A surrounded by the elastic contact pieces 32.

The leading end portion 325 extends from a front end of the contact portion 324 (the edge on the opposite side to the base portion 323) and is positioned outward of the contact portion 324 in a direction orthogonal to the central axis C. Specifically, the leading end portion 325 is inclined with respect to the central axis C so as to be away from the central axis C as it advances from the contact portion 324 toward the front side (see FIG. 3).

The connector terminal 1 configured as above is used by, for example, being connected to the leading end of the electric wire 9 having the core wire 90 made of conductive fibers such as carbon fibers, as shown in FIG. 6. Specifically, the connector terminal 1 is connected to the electric wire 9 as follows. Note that in the electric wire 9 of this embodiment, the core wire 90 is formed of carbon fibers of several micrometers in diameter that are bundled together.

The electric wire 9 is connected to the electric wire connector 2 of the connector terminal 1. Specifically, the end portion of the electric wire 9 with the core wire 90 exposed is placed on the body 21 of the electric wire connector 2. Subsequently, the conductive crimping pieces 22 (the first crimping pieces 221 and the second crimping pieces 222) are crimped to embrace the core wire 90, which causes the core wire 90 to be press-contacted to the body 21. At this time, crimping is performed so that the rear side (the lower side in FIG. 6) edge of the other second crimping piece 222B is not pressed by a crimping jig and thereby not fully laid on (i.e. is slightly raised from) the core wire 90 side. Then, the sheathed part crimping pieces 23 are crimped to sandwich the insulated portion of the electric wire 9 between the sheathed part crimping pieces 23 and the body 21. The connector terminal 1 is thus connected to the electric wire.

The material of the core wire 90 of the electric wire 9 connected to the connector terminal 1 is not limited to carbon fibers. The core wire 90 may be of; resin fibers with metal filler; plated fibers such as polyester fibers, carbon fibers, or the like that are metal plated; and conductive fibers such as fibers of polypyrroles, polythiophenes, polyacetylenes, polyphenylenes, polyphenylene vinylenes, polyanilines, polyacenes, polythiophene vinylenes, and a copolymer of two or more of these polymers. That is, according to the connector terminal 1 of this embodiment, the electric wire 9 in the electric wire connector 2 obtain sufficient pull-out strength even in the case where the core wire 90 is constituted by bundles of such conductive fibers as carbon fibers that are extremely thin and not internally stressed at the time of crimping. The electric wire connector 2 can also obtain sufficient pull-out strength even in the case where the core wire 90 is constituted by other conductive fibers. The connector terminal 1 is also connectable to an electric wire having a metal core wire.

Figure 9:
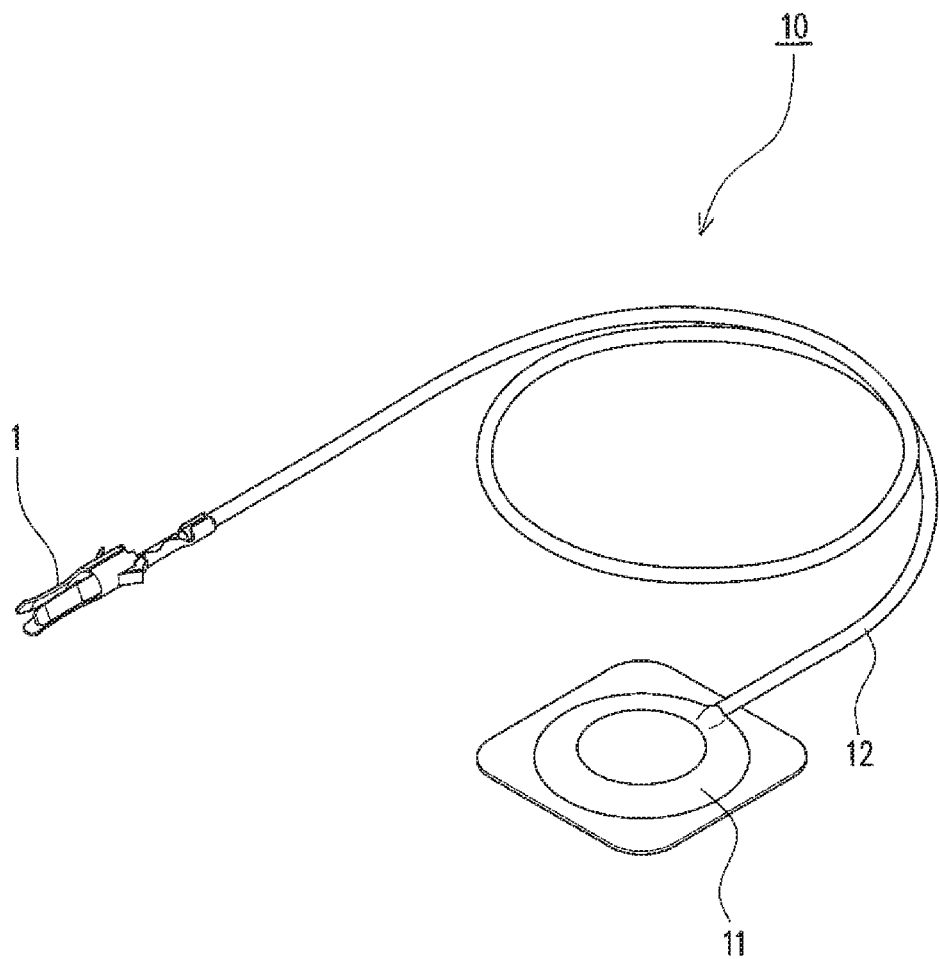
FIG. 9 is an explanatory view for a medical device sensor.

The connector terminal 1 may also be used, for example, for medical device sensors or the like. The medical device sensor of this embodiment is, for example, an electrocardiographic electrode 10 as shown in FIG. 9. The electrocardiographic electrode 10 includes an electrode body 11 that is attached to, for example, the skin of a chest of a medical examinee or the like, an output electric wire 12 extending from the electrode body 11, and the connector terminal 1 connected to a leading end of the output electric wire 12.

Figure 10:
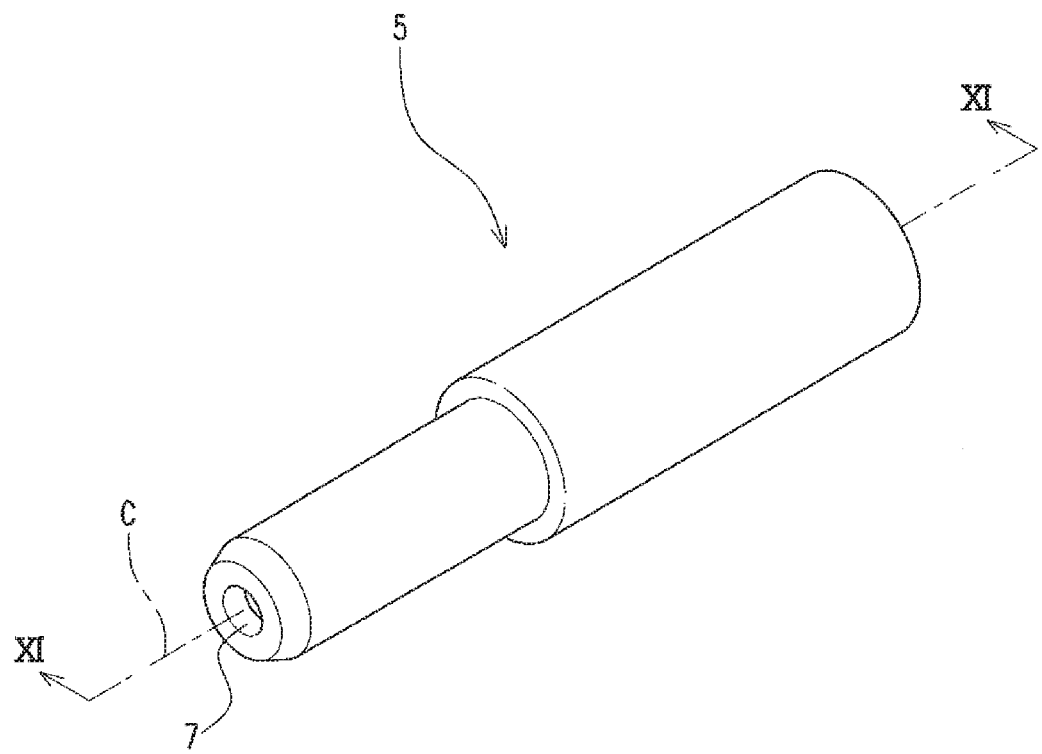
FIG. 10 is a perspective view of a connector housing.

Note that the connector terminal 1 may be used, for example, while being housed in the connector housing 5 shown in FIG. 10, or the like.

According to the connector terminal 1 configured as above, the clearance between the first crimping piece 221B and the second crimping piece 222B (the first clearance $\alpha$) that is formed at the position closest in the direction of the central axis C to the insulation sheathed member 91 of the electric wire 9 is large when the electric wire 9 in which the core wire 90 is constituted by the conductive fibers is connected to the connector terminal 1 (the electric wire connector 2) by crimping the conductive crimping pieces 22 (the first crimping pieces 221 and the second crimping pieces 222), as shown in FIG. 6. This configuration suppresses the conductive fibers from being broken at the aforementioned portion, thereby obtaining sufficient pull-out strength. A more specific description is provided below.

If the clearance between the first crimping piece 221 and the second crimping piece 222 is small when the conductive crimping pieces 22 are crimped to connect the electric wire 9 to the connector terminal 1, the conductive fibers are likely to be broken between the first crimping piece 221 and the second crimping piece 222 (along the boundary therebetween) as a result of, for example, biting of the conductive fibers between the first crimping piece 221 and the second crimping piece 222 at the time of crimping. Even if the conductive fibers are broken at another position between the first crimping piece 221A or 221B and the second crimping piece 222A, sufficient pull-out strength of the conductive fibers is obtained by prevention of the conductive fibers from being broken between the other first crimping piece 221B and the other second crimping piece 222B at the time of crimping. Therefore, sufficient pull-out strength is obtained through the configuration having the first clearance $\alpha$ wider than the second clearance $\beta$ (specifically, making the first clearance $\alpha$ wide enough to avoid breaking the conductive fibers due to the biting or the like) to suppress the breakage at the position of the clearance $\alpha$.

Even if the breakage occurs at a position where any of the second clearances $\beta$ is formed, sufficient electric conduction is realized between the electric wire 9 (the core wire 90) and the connector terminal 1 as long as the first crimping pieces 221A and 221B and the second crimping piece 222A are strongly crimped to firmly embrace the core wire 90.

In the connector terminal 1 of this embodiment, the first clearance (the clearance between the other first crimping piece 221B and the other second crimping piece 222B) a has such a distance that the other first crimping piece 221B and the other second crimping piece 222B having their edges expanding as a result of crimping are not in contact with each other, in the state where the electric wire 9 is connected to the connector terminal 1 (i.e., in the state where the crimping pieces 221A, 221B, 222A, and 222B are crimped). Thus, the breakage of the conductive fibers is more reliably suppressed at a position (boundary) between the first crimping piece 221B and the second crimping piece 222B, the position being located closest in the direction of the central axis C to the insulation sheathed member 91 of the electric wire 9. This consequently secures sufficient pull-out strength more reliably.

In the connector terminal 1 of this embodiment, for example, each of an edge between the distal end 2211B and the proximal end 2212B of the first crimping piece 221B and an edge between the distal end 2221A and the proximal end 2222B of the second crimping piece 222A extends in a direction crossing the width direction of the body 21.

According to such a configuration, in the state where the crimping pieces 221B and 222A are crimped, the edges of the crimping pieces 221B and 222A come into contact with the conductive fibers (the conductive fibers constituting the core wire 90) so as to cross them diagonally. This configuration increases the area of contact of the crimping pieces with the conductive fibers compared to the case where these edges are in contact with the conductive fibers so as to cross them orthogonally (in the width direction of the body 21), which as a result further suppresses the conductive fibers from being broken along the edges.

In the electric wire 9 to which the connector terminal 1 configured as above is connected (i.e., the electric wire with the connector terminal), the electric wire 9 in the electric wire connector 2 of the connector terminal 1 obtains sufficient pull-out strength even if the electric wire 9 having the core wire 90 constituted by conductive fibers is press-contacted to the electric wire connector 2.

That is, in the case where the connector terminal 1 is used for the medical device sensor 10, the electric wire 9 in the electric wire connector 2 of the connector terminal 1 obtains sufficient pull-out strength even if an electric wire having a core wire constituted by conductive fibers is used in the medical device sensor 10 as an output electric wire.

It is a matter of course that the crimp terminal, the electric wire with the crimp terminal, and the medical device sensor of the present invention are not limited to the aforementioned embodiment, but various modifications can be made without departing from the gist of the present invention. For example, a configuration of an embodiment may be added to a configuration of another embodiment, and part of a configuration of an embodiment may be replaced by a configuration of another embodiment. Further, part of a configuration of an embodiment may be deleted.

In the connector terminal 1 of the aforementioned embodiment, the conductive crimping pieces 22 are constituted by the two first crimping pieces 221 and the two second crimping pieces 222, without limitation thereto. The conductive crimping pieces 22 may be constituted by two or more first crimping pieces 221 and at least one second crimping piece 222. The two or more first crimping pieces 221 and the at least one second crimping piece 222 are alternately arranged while being displaced from each other in the direction of the central axis C.

A specific configuration of the electric connector 3 of the crimp terminal is not limited to the aforementioned embodiment. The electric connector 3 of the crimp terminal (the connector terminal) 1 of the aforementioned embodiment is configured to retain the mating terminal pin P using three or more elastic contact pieces 32, without limitation thereto. The electric connector 3 may be configured to be connected to the mating terminal by a fastener member, soldering, or the like.

The connector terminal 1 may be housed in a connector housing to configure a connector. An example of the configuration of the connector is described as follows.

Figure 11:
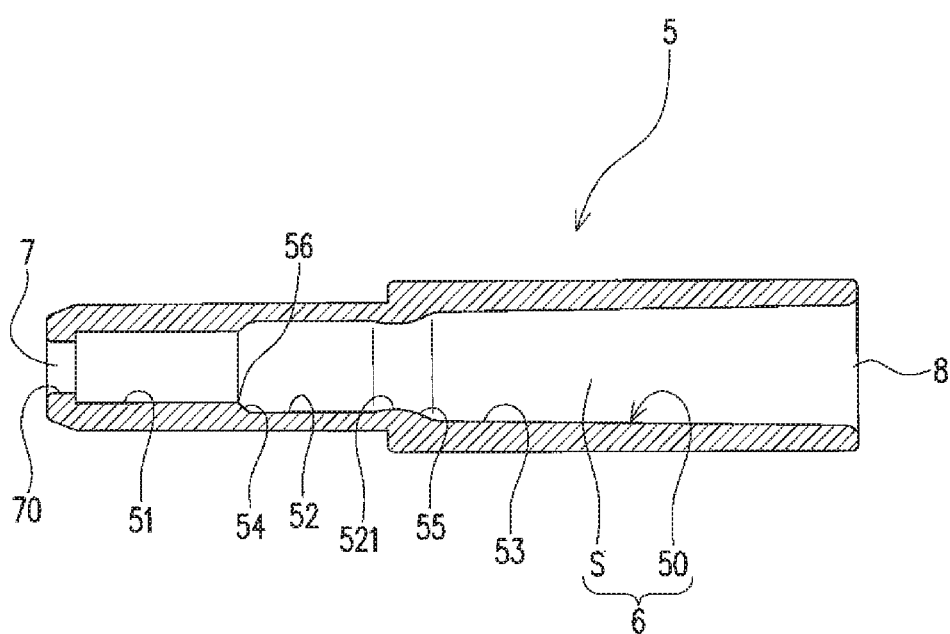
FIG. 11 is a cross sectional view taken along line XI-XI in FIG. 10.
Figure 12:
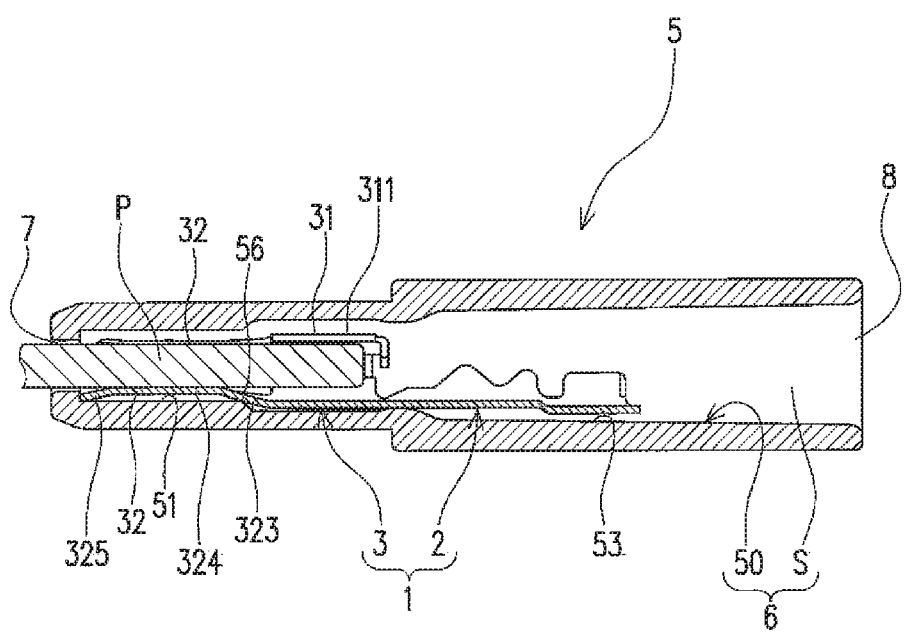
FIG. 12 is a cross sectional view of the connector in a state of being connected to the mating terminal pin.
Figure 13:
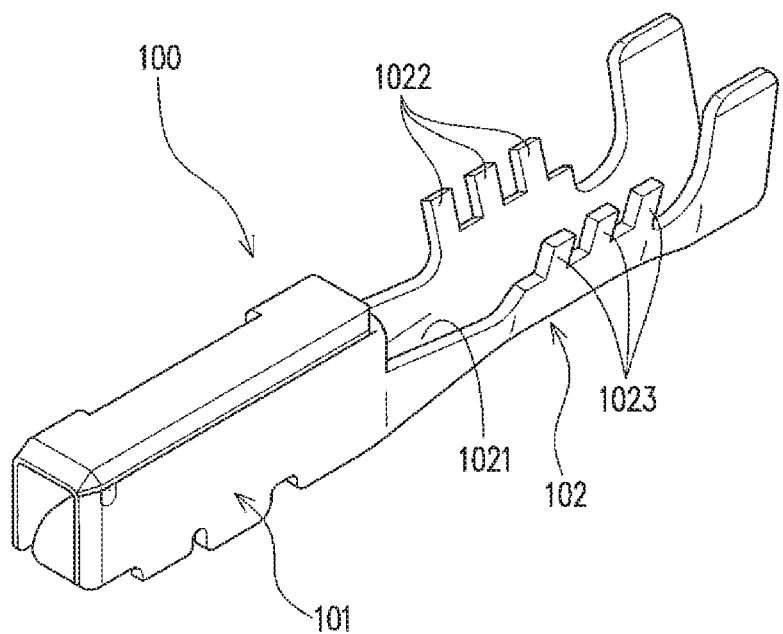
FIG. 13 is a perspective view of a conventional connector terminal.
Figure 13:
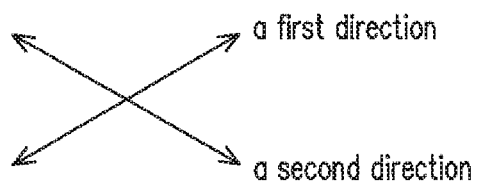
Figure 14:
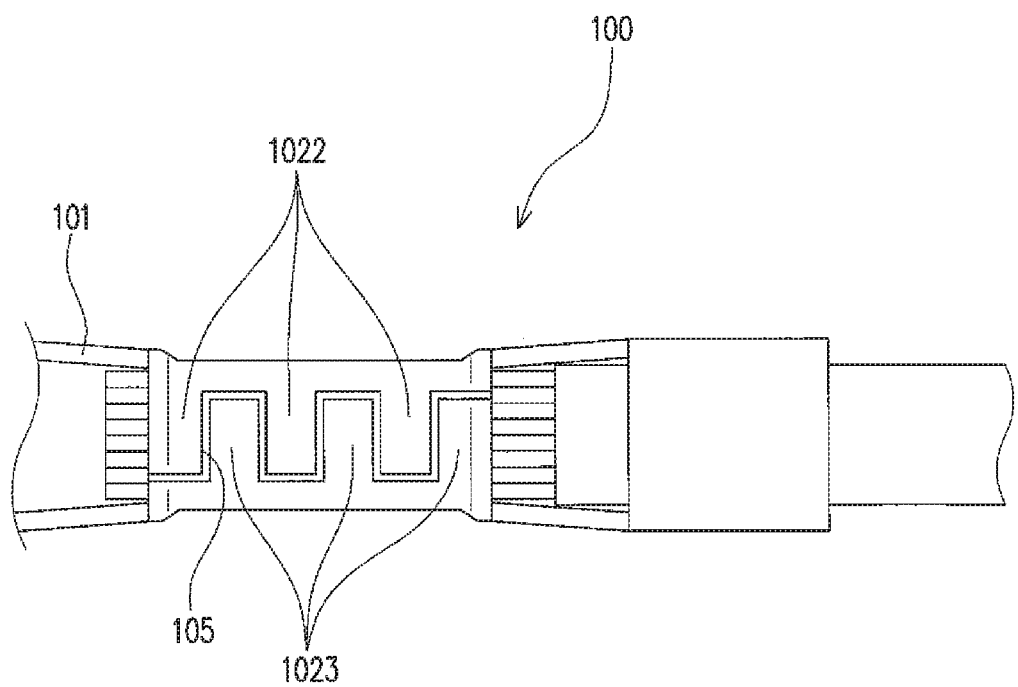
FIG. 14 is a view showing the a where an electric wire is connected to the connector terminal.
Figure 15:
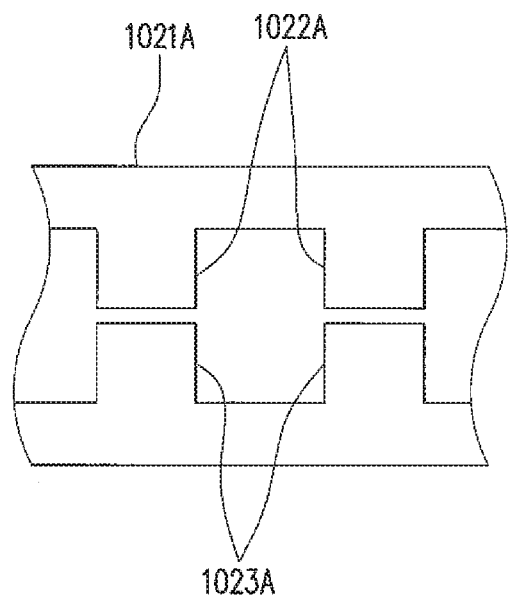
FIG. 15 is a view showing a state where an electric wire is connected to another conventional connector terminal.

As shown in FIG. 10 to FIG. 12, the connector housing 5 includes a terminal housing portion 6 in which the connector terminal 1 is housed, and a terminal insertion port 7 through which the mating terminal pin P is inserted. The connector housing 5 also has a rear end opening 8 through which the connector terminal 1 is inserted. A more specific description is provided below. Hereinafter, in the direction of the central axis C, the terminal insertion port 7 side is referred to as a front side, and the rear end opening 8 side is referred to as a rear side.

The connector housing 5 has a tubular shape having the central axis C, and is formed of an insulating resin. The connector housing 5 has an inner surface 50. The inner surface 50 defines a space (a housing space) S in which the connector terminal 1 is housed. The terminal housing portion 6 of this embodiment has the inner surface 50 and the housing space S. The terminal insertion port 7 is configured to communicate the housing space S with the outside in the direction of the central axis C at the front end of the connector housing 5. The rear end opening 8 is configured to communicate the housing space S with the outside in the direction of the central axis C at the rear end of the connector housing 5.

The inner surface 50 of this embodiment defines a circular or substantially circular cross section at every position in the direction of the central axis C (cross section in a surface direction orthogonal to the central axis C of the inner surface 50). The inner surface 50 defines a plurality of portions having different diameters. Specifically, the inner surface 50 has, in order from the front side to the rear side, a first portion 51 having a smallest diameter, a second portion 52 having a greater diameter than the first portion 51, and a third portion 53 having a greater diameter than the second portion 52 (having a greatest diameter). The first portion 51 and the second portion 52 are connected to each other through a first reduced diameter portion 54 that has a diameter reduced as it advances toward the front side. The second portion 52 and the third portion 53 are connected to each other through a second reduced diameter portion 55 that has a diameter reduced as it advances toward the front side. The portions 51 to 55 that are defined by the inner surface 50 share the same central axis.

The first portion 51, the first reduced diameter portion 54, and the second portion 52 are configured to enclose the electric connector 3 through the inner surface 50. The second portion 52 has a housing side engagement portion 521 configured to engage with the terminal side engagement portions 313 at a position corresponding to the terminal side engagement portions 313 of the electric connector 3 (specifically, the electric connector body 31). The housing side engagement portion 521 of this embodiment is defined by partial reduction of the diameter of the inner surface 50, which is provided in the direction of the central axis C, that is, a portion projecting toward the central axis C, and is provided at a position adjacent to (continuous with) the second reduced diameter portion 55 in the direction of the central axis C. A boundary portion 56 between the first portion 51 and the first reduced diameter portion 54 abuts the base portions 323 of the elastic contact pieces 32 from the outside thereof (specifically, the outside in the radial direction of the inner surface 50). That is, the boundary portion 56 supports the base portions 323 from the outside.

The rear end portion of the third portion 53 defines the rear end opening 8 that is formed in the rear end portion of the connector housing 5. The housing space S of the connector housing 5 and the outside space communicate with each other through the rear end opening 8.

The connector housing 5 has a projecting portion 70 that projects from the first portion 51 at a certain position in the direction of the central axis C toward the central axis C. The projecting portion 70 of this embodiment is a wall portion (a front end wall portion) that defines the terminal insertion port 7 at the front end of the connector housing 5. That is, the projecting portion 70 projects from the end edge on the front end side of the first portion 51 toward the central axis C. The projecting portion 70 is provided at a position at which it abuts the leading end portions 325 of the connector terminal 1 housed in the connector housing 5 as a result of the insertion of the mating terminal pin P through the terminal insertion port 7 into the connector housing 5, which causes the contact portions 324 pressed by the mating terminal pin P to be elastically deformed from a curved form to a flat form. A more specific description is provided below.

In the state before the mating terminal pin P is inserted (the initial state), the contact portions 324 of the elastic contact pieces 32 are curved to project toward the central axis C. When the mating terminal pin P is inserted through the terminal insertion port 7 in the direction of the central axis C in this state, the mating terminal pin P, as it advances toward the rear side, presses the contact portions 324 of the elastic contact pieces 32 radially outward of the inner surface 50, since the inscribed circle y (see FIG. 2) is smaller than the outer circumference of the mating terminal pin P. That is, the contact portions 324 of the elastic contact pieces 32 are subjected to a pressing force of the mating terminal pin P exerted radially outward of the inner surface 50.

At this time, the rear ends of the contact portions 324 are restricted from moving since they are connected to the base portions 323 that extend from the electric connector body 31 engaging with the connector housing 5 and that are supported by the boundary portion 56 from the outside in the radial direction of the inner surface 50. Thus, the front end edges of the contact portions 324 subjected to the pressing force move toward the terminal insertion port 7, which thereby elastically deforms the contact portions 324 to make their curvature small. When the mating terminal pin P is fully inserted, the contact portions 324 are deformed from the curved form to the flat form along the mating terminal pin P.

When the contact portions 324 are elastically deformed to have the flat form, the leading end portions 325 are restricted by the first portion 51 from moving radially outward of the inner surface 50, but move toward the front end (the terminal insertion port 7 side) while being in contact with the first portion 51 since they are capable of moving along the first portion 51. That is, the leading end portions 325 slide (move while sliding) toward the terminal insertion port 7 with respect to the first portion 51. When the contact portions 324 are elastically deformed to have the flat form to conform to the mating terminal pin P (see FIG. 12), the leading end portions 325 having slid toward the terminal insertion port 7 with respect to the first portion 51 abut the projecting portion 70. In the state where the contact portions 324 have been elastically deformed to have the flat form as aforementioned, the entire areas of the contact portions 324 in the direction of the central axis C are in contact with the mating terminal pin P.

As a result, in the connector (the connector housing 5 with the connector terminal 1 housed therein), a sufficient force for retaining the mating terminal pin P is obtained by a retaining force resulting from an elastic restoring force of the elastic contact pieces 32 (the pressing force applied to the mating terminal pin P) and a frictional force resulting from the contact between the contact portions 324 and the mating terminal pin P through the entire areas of the contact portions 324 in the direction of the central axis C, that is, in the insertion direction (force against the mating terminal pin P that is being pulled out). In addition, the connector configured as above requires a smaller elastic restoring force (the pressing force of the elastic contact pieces 32 applied to the mating terminal pin P) than in the case where a force for retaining the mating terminal pin P is obtained only by the elastic restoring force. This enables ease of inserting the mating terminal pin P into the connector.

That is, while a mating terminal pin is hard to be inserted into a connector that is configured to obtain a force for retaining the mating terminal pin using only the elastic restoring force of elastic contact pieces, the aforementioned connector is configured to obtain the force for retaining the mating terminal pin P using the frictional force in addition to the elastic restoring force, which, as a result, enables both ease of inserting the mating terminal pin P into the connector and obtaining a sufficient force for retaining the mating terminal pin P that has been inserted.

The medical device sensor of the aforementioned embodiment is an electrocardiographic electrode, without limitation thereto. The medical device sensor may be, for example, a blood pressure sensor, an SpO2 (arterial oxygen saturation) sensor, an expiration sensor, and the like.

The connector terminal 1 is connectable to an electric wire that is used for a variety of devices, not limited to the medical device sensor, and that has a core wire made of conductive fibers.

The crimp terminal, the electric wire with the crimp terminal, and the medical device sensor of this embodiment are as described above, but the present invention is not limited to the aforementioned embodiment, and the design can be appropriately modified within the scope intended by the present invention. The operational advantages of the present invention are also not limited to the foregoing embodiments. That is, the embodiments disclosed herein should be construed in all respects as illustrative but not limiting. The scope of the present invention is not indicated by the foregoing description but by the scope of the claims. Further, the scope of the present invention is intended to include all the modifications equivalent in the sense and the scope of the claims.

What is claimed is:

1. A crimp terminal, comprising:
an electric wire connector connectable to an electric wire having a core wire sheathed with an insulating member, the electric wire connector comprising: a body extending in a first direction that coincides with an extending direction of a portion of the electric wire to which the electric wire connector is connected; a plurality of first crimping pieces extending from a first end in a second direction orthogonal to the first direction of the body; and at least one second crimping piece extending from a second end in the second direction of the body,
wherein the plurality of first crimping pieces and the at least one second crimping piece are alternately arranged while being displaced from each other in the first direction, and are configured to be crimped to embrace the core wire exposed in a leading end portion of the electric wire so that the core wire is press-contacted to the body, and
wherein, when the plurality of first crimping pieces and the at least one second crimping piece are crimped to connect the core wire to the electric wire connector, a first clearance in the first direction between one of the plurality of first crimping pieces and the at least one second crimping piece, the first clearance being formed at a position closest in the first direction to the insulating member of the electric wire, is larger than a second clearance in the first direction between a remaining one of the plurality of first crimping pieces and the at least one second crimping piece, the second clearance being formed at another position in the first direction.

2. The crimp terminal according to claim 1, wherein
the first clearance has such a distance that the one of the plurality of first crimping pieces and the at least one second crimping piece having their edges expanding as a result of crimping are not in contact with each other.

3. The crimp terminal according to claim 1, wherein
each of the plurality of first crimping pieces has a distal end portion, a proximal end portion, and an edge extending in a direction crossing the second direction between the distal end portion and the proximal end portion of each of the plurality of first crimping pieces, and
the at least one second crimping piece has a distal end portion, a proximal end portion, and an edge extending in a direction crossing the second direction between the distal end portion and the proximal end portion of the at least one second crimping piece.

4. An electric wire arrangement comprising:
the crimp terminal according to claim 1; and the electric wire connected to the electric wire connector of the crimp terminal, wherein the core wire is constituted by conductive fibers.

5. A medical device sensor, comprising:
a medical sensor body; an output electric wire extending from the medical sensor body; and the crimp terminal according to claim 1, wherein
the output electric wire is connected to the electric wire connector of the crimp terminal, and
the output electric wire has a core wire constituted by conductive fibers.

* * * * *